(12) United States Patent
Le Campion et al.

(10) Patent No.: US 6,582,952 B1
(45) Date of Patent: Jun. 24, 2003

(54) METHOD FOR ELIMINATING A NITROGENATED HETEROCYCLIC, OR AROMATIC, COMPOUND IN AN EFFLUENT

(75) Inventors: Laurence Le Campion, Monts (FR); Jamal Ouazzani, Massy (FR)

(73) Assignees: Centre National de la Recherche Scientifique, Paris (FR); Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/509,158

(22) PCT Filed: Sep. 21, 1998

(86) PCT No.: PCT/FR98/02011

§ 371 (c)(1),
(2), (4) Date: Jun. 6, 2000

(87) PCT Pub. No.: WO99/15465

PCT Pub. Date: Apr. 1, 1999

(30) Foreign Application Priority Data

Sep. 22, 1997 (FR) .............................................. 97 11757

(51) Int. Cl.[7] .................................................. C12P 13/00
(52) U.S. Cl. ................................ 435/262.5; 435/252.5; 435/170; 435/121
(58) Field of Search .............................. 435/121, 262.5, 435/170, 252.5

(56) References Cited

PUBLICATIONS

Smith, et al., Arch. Biochem. (1950), 28, 232–41.*
ATCC Catalogue of Bacteria, 1992, pp. 42–43.*

\* cited by examiner

*Primary Examiner*—Irene Marx
(74) *Attorney, Agent, or Firm*—Burns, Doane, Swecker & Mathis L.L.P.

(57) ABSTRACT

This invention relates to a method for the removal of a nitrogen containing heterocyclic or aromatic compound, comprising at least one nitro group, in an effluent by the conversion of said, at least one nitro group into an amine group by means of a reducing agent. The reducing agent can be hydrogen in the presence of Pd/C or a micro-organism.

This invention also relates to a method for the synthesis of 5-amino-1,2,4-triazole-3-one from 5-nitro-1,2,4-triazole-3-one by said method of conversion, that allows one to achieve synthesis yields greater than 80%.

This invention also relates to a colony of the type *Bacillus licheniformis* capable of converting one or more nitro groups of nitrogen containing heterocyclic compounds into one or more amine groups. This colony has been filed in the CNCM, held by the Pasteur Institute, under the number I-1915.

10 Claims, 2 Drawing Sheets

METHOD FOR ELIMINATING A NITROGENATED HETEROCYCLIC, OR AROMATIC, COMPOUND IN AN EFFLUENT

TECHNICAL FIELD OF THE INVENTION

This invention relates to a method for the removal of a nitrogen containing heterocyclic or aromatic compound, comprising at least one nitro group. The method of the invention consists of converting at least one nitro group into an amine group by means of a reducing agent. The reducing agent can be a micro-organism capable of reducing said, at least one nitro group into an amine group, or can be hydrogen in the presence of a Pd/C catalyst.

This invention also relates to a method for the synthesis of 5-amino-1,2,4-triazole-3-one from 5-nitro-1,2,4-triazole-3-one by said method of conversion.

This invention also relates to a colony of the type *Bacillus licheniformis* capable of converting one or more nitro groups of nitrogen containing heterocyclic compounds into one or more amine groups.

The nitrogen containing heterocyclic compound can be, for example, a triazine or a triazole. These compounds constitute a heterogeneous family of nitrogen containing molecules several of which are used in industry and in agriculture. Although the toxicity of these compounds has not always been given prominence, they can nevertheless constitute a source of pollution, when released into the natural environment.

An example of such a compound is ONTA or 1,2-dihydro-5-nitro-1,2,4-triazole-3-one. This compound is explosive and it can reach concentrations of about 15 g/l in certain solutions such as industrial processing effluents stemming from the manufacture of explosives. These effluents are pollutants according to the legislation currently in force and are at present being stored in this state while awaiting a suitable treatment process.

The method of the invention enables precisely such solutions to be treated, solutions comprising, in particular, a compound such as ONTA, that is to say an explosive nitrogen containing heterocyclic compound, comprising at least one nitro group, by converting this explosive nitrogen containing heterocyclic compound into a non-explosive compound.

In the example mentioned above, the method of the invention allows one to convert the nitro group of the ONTA into an amine group to form 5-amino-1,2,4-triazole-3-one.

Furthermore, the 5-amino-1,2,4-triazole-3-one formed is a compound of value, since it can be a precursor for the synthesis of compounds, having, for example antiviral activity such as ribavirine, and pirazomicine, an inhibiting activity for the NO-synthases (N.O.S.) such as 3-amino-1,2,4-triazine and aminoguanidine, a herbicide activity such as 5-amino-1,2,4-triazole, an anti-parasitic activity and a cytotoxic activity.

The method of the invention therefore makes it possible, in certain cases to convert a compound of no value into a compound of value.

Another aspect of the method of the invention is the synthesis of the heterocyclic amine 5-amino-1,2,4-triazole-3-one from 5-nitro-1,2,4-triazole-3-one.

The aromatic compound comprising at least one nitro group can be, for example, a benzene ring with one or more nitro groups, for example a compound chosen from the group comprising 2,6-dinitroaniline, 1,3-dinitrobenzene, 2-nitroaniline and ortho-, meta- and para-nitrobenzoic acids.

The aromatic amines and nitrogen containing heterocyclic amines are often obtained by reduction of the nitrated analogue. This reduction is catalyzed by various methods using reducing agents such as zinc, iron or tin, in an acid medium or hydrides such as lithium aluminum hydride, or catalytic hydrogenation. However, when the aromatic amines are complex, that is to say when they include sensitive functional groups apart from the nitro group, numerous secondary reactions can occur on these groups that then reduces the yield of the synthesis of the targeted aromatic amine.

For example, the reduction of ONTA by catalytic hydrogenation in the presence of platinum oxide can affect the aromaticity of the molecule in addition to the nitro group.

Furthermore, the experimental conditions for these synthesis methods are often drastic and dangerous.

DESCRIPTION OF THE INVENTION

This invention relates to a method for the at least partial removal of at least one nitrogen containing heterocyclic compound or aromatic compound comprising at least one nitro group, present in an effluent, said method comprising the following steps:

bringing the solution of the nitrogen containing heterocyclic compound or aromatic compound to be removed into contact with a reducing agent in order to convert said nitro group or groups of the heterocyclic compound or aromatic compound into one or more amine groups, and separation of the reducing agent from the solution of the nitrogen containing heterocyclic compound or aromatic compound, at least a part of whose nitro groups has been converted into amine groups.

According to the method of the invention, the solution of the nitrogen containing heterocyclic compound or aromatic compound comprising at least one nitro group can contain a single compound or several different compounds. This solution can be an industrial processing effluent arising from the manufacture of explosives, an industrial effluent, foul water and more generally a solution comprising nitrogen containing heterocyclic compounds or aromatic compounds comprising at least one nitro group that it is necessary to treat by converting one or more nitro groups into amine groups. This solution will also be referred to in what follows as the solution to be treated, and the nitrogen containing heterocyclic compound or aromatic compound comprising at least one nitro group will also be referred to in what follows, respectively as a nitrogen containing heterocyclic compound to be treated or an aromatic compound to be treated.

According to the method of the invention, the reducing agent can be hydrogen in the presence of a Pd/C catalyst.

The hydrogenation catalyst Pd/C, or palladium on carbon, can be used at a quantity of from 5 to 15% by weight with respect to the quantity of nitrogen containing heterocyclic compound or aromatic compound to be removed, preferably at a quantity of 10% by weight. The effluent can, for example, be an aqueous solution or methanol.

According to the method of the invention, the reducing agent can be a micro-organism.

According to the method of the invention, the nitrogen containing heterocyclic compound comprising at least one nitro group can be a triazole.

According to the method of the invention, when the nitrogen containing heterocyclic compound to be treated is a triazole, it can be a compound with the following formula (I):

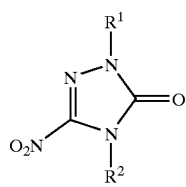

(I)

in which the $R^1$ and $R^2$ groups, which can be identical or different, represent H, or a substituent group chosen from within the group comprising —$NO_2$, —OH, —COOH, —Cl, —$NH_2$, or a cyclic or linear glucose unit, non-substituted or substituted by one or more groups chosen independently from within the group comprising for example an acetyl or a tolyl group or a linear or cyclic alkyl group, comprising from 1 to 10 atoms of carbon, non-substituted or substituted by one or more groups chosen independently from within the group comprising —$NO_2$, —OH, —COOH, —Cl, —$NH_2$. For example, when $R_1$ and/or $R_2$ is a glucose unit, it can be ribose, deoxyribose, etc non-substituted or substituted.

According to the method of the invention, the compound of formula (I) can be converted into a compound with the following formula (II):

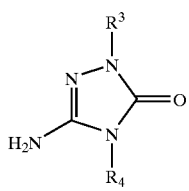

(II)

in which the groups $R^3$ and $R^4$, which can be identical or different, represent H, a substituent group chosen from within the group comprising —$NO_2$, —OH, —COOH, —Cl, —$NH_2$, or a cyclic or linear glucose unit, non-substituted or substituted by one or more groups chosen independently from within the group comprising for example an acetyl or a tolyl group or a linear or cyclic alkyl group, with 1 to 10 atoms of carbon, non-substituted or substituted by one or more groups chosen independently from among —$NO_2$, —OH, —COOH, —Cl, —$NH_2$. For example, when $R_1$ and/or $R_2$ is a glucose unit, it can be ribose, deoxyribose, β-D-ribofuranosyl, etc.

When $R^1$ is a —$NO_2$ group, this group can be reduced to the corresponding amine and $R^3$ can then be an —$NH_2$ group. Similarly, when $R^2$ is a —$NO_2$ group, this group can be reduced to the corresponding amine and $R^4$ can then be an —$NH_2$ group.

The aromatic compound comprising at least one nitro group to be treated can be for example, a mono-, di- or tri-nitrobenzene, 2-nitroaniline and ortho-, meta- and para-nitrobenzoic acids.

For example, when 2,6-dinitroaniline is treated, one can obtain 2-amino-6-nitroaniline, when 1,3-dinitrobenzene is treated, one can obtain 1-amino-3-nitrobenzene, when 2-nitroaniline is treated, one can obtain 2-aminoaniline and when the ortho-, meta- and para-nitrobenzoic acids, one can obtain ortho-, meta- and para-aminobenzoic acids respectively.

According to the invention, the micro-organism capable of converting said nitro group or groups into an amino group or groups can be selected by the screening of micro-organisms that are living or which could live, in an industrial processing effluent arising from the manufacture of explosives, in foul water, and more generally in a medium, referred to below as the source medium, comprising nitrogen containing heterocyclic compounds comprising preferably at least one nitro group. For example, the screening can be carried out starting with a sample that can be treated according to the method of the invention, for example a sample from an industrial processing effluent arising from the manufacture of explosives, or from purification water that includes organic compounds that comprise nitro groups, nitrated aromatic compounds, nitrogen containing heterocyclic compounds etc.

According to the method of the invention, the micro-organism capable of converting said nitro group or groups into an amine group or groups can be selected from a laboratory collection.

According to the method of the invention, the selection by screening can be carried out, for example, from a culture of micro-organisms living in a source medium such as those mentioned above. This culture is preferably carried out on a rich culture medium, in a way that enables life to be maintained and that enables one to cultivate a maximum of the micro-organisms present in this source medium. Moreover, the culture medium is preferably solid so that the micro-organisms can form colonies.

An example of a rich culture medium for the selection by screening is a medium that comprises for 1 liter of water:

| $K_2HPO_4$ | 1 g | | |
|---|---|---|---|
| $KH_2PO_4$ | 0.5 g | $NaNO_3$ | 2 g |
| glucose | 30 g | KCl | 0.5 g |
| maize liquor | 10 g | $FeSO_4$ | 0.02 g |
| $MgSO_4$ | 0.5 g | | |

The medium is sterilized at 120° C. for 20 minutes before use.

When the number of micro-organisms is too great in the source medium, the culture of these micro-organisms on a rich solid culture medium will be preceded by a dilution of a sample of the source medium so as to be able to form isolated colonies of these micro-organisms.

An analysis of the capacity of each of the colonies formed on the rich solid medium to reduce nitro groups of nitrogen containing heterocyclic compounds to be treated and an analysis of the biochemical nature of each of these colonies respectively enables one to give prominence to and to identify the micro-organisms that can be used in accordance with the method of the invention.

Preferably, according to the invention, the micro-organism is a micro-organism that is widespread in the natural environment and does not manifest any particular toxicity.

According to the invention, the micro-organism, in addition to converting one or more nitro groups of nitrogen containing heterocyclic compounds or aromatic compounds into an amine group, can metabolize the nitrogen containing heterocyclic compound or aromatic compound comprising said amine group or groups in such a way that this compound is partially or totally degraded.

The micro-organism can, for example, be one or more filamentous fungi and/or one or more bacteria.

When the micro-organism is a bacterium, it may be of the *Bacillus licheniformis* type.

The preferred *Bacillus licheniformis* can be the *Bacillus licheniformis* colony LCM2 filed with the Collection Nationale de Cultures de Microoganismes (CNCM), Institut Pasteur, located at 25, Rue du Docteur Roux, F-75724 Paris Cedex 15, France. The deposit was filed Nov. 18, 1997 under the accession number I-1915 for the deposit.

According to the method of the invention, the micro-organism *Bacillus licheniformis* is, for example, suitable for the conversion of the nitrogen containing heterocyclic compound to be treated with the following formula (III):

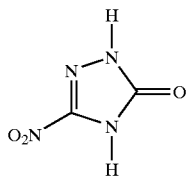
(III)

into a nitrogen containing heterocyclic compound with the following formula (IV):

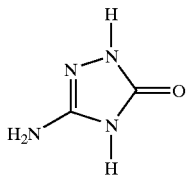
(IV)

According to the method of the invention, bringing the solution of said nitrogen containing heterocyclic compound to be treated into contact with a micro-organism capable of reducing said nitro group or groups into amine groups is carried out by mixing a biomass of said micro-organism with said solution.

The biomass of the micro-organism can be obtained through a culture of the one or more micro-organisms selected by screening, in a rich, solid or liquid culture medium, preferably a liquid culture medium.

A rich medium that can be used to develop the biomass, when the micro-organism is *Bacillus licheniformis* is a medium comprising, for a liter of water:

| | | | |
|---|---|---|---|
| $K_2HPO_4$ | 1 g | | |
| $KH_2PO_4$ | 0.5 g | | |
| glucose | 30 g | $NaNO_3$ | 2 g |
| maize liquor | 10 g | KCl | 0.5 g |
| $MgSO_4$ | 0.5 g | $FeSO_4$ | 0.02 g |

The medium is sterilized at 120° C. for 20 minutes before use.

When a sufficient quantity of biomass is obtained, and when the culture medium is a liquid, this biomass can be recovered by compacting it by centrifugation of the culture medium.

According to the method of the invention, the biomass can be obtained from one or more types of micro-organisms capable of reducing one or more nitro groups into amine groups in accordance with the method of the invention.

The biomass mixed with the solution of nitrogen containing heterocyclic compound to be treated for the bringing into contact must be in a sufficient quantity to allow the conversion of the one or more nitro groups of the nitrogen containing heterocyclic compounds or aromatic compounds to be treated which are present in this solution. The quantity of biomass to be used can be determined, for example, as a function of the quantity of compounds that comprise nitro groups to be converted into amine groups. This quantity of biomass may also be determined by means of tests in which the quantity for conversion of nitro groups of a nitrogen containing heterocyclic compound present in a solution is measured in relation to the quantity of biomass of micro-organism mixed with this solution, the concentration of nitrogen containing heterocyclic compounds to be treated, the duration of the tests being identical for each test.

The biomass can be mixed with the solution of nitrogen containing heterocyclic compound to be treated by means of a traditional stirrer, for example a rotary stirrer, at a stirring speed that can range from 50 to 250 rpm, for example 100 rpm.

The stirring can be maintained for the entire duration of the contact between the biomass of a micro-organism and the nitrogen containing heterocyclic compound to be treated in a manner that optimizes this bringing into contact. The mixture of biomass and solution of the nitrogen containing heterocyclic compound to be treated is also referred to below as the incubation mixture.

Preferably, according to the method of the invention, the solution of the nitrogen containing heterocyclic compound comprising at least one nitro group, or the incubation mixture, can be neutralized to a pH value that permits the conversion of the one or more nitro groups into amine groups.

A series of tests consisting of measuring the quantity of compounds comprising nitro groups converted in an incubation mixture as a function of the pH can enable one to determine a pH range that permits this conversion, that is to say, favors this conversion.

For example, when the micro-organism is *Bacillus licheniformis*, the pH of the solution of the nitrogen containing heterocyclic compound comprising at least one nitro group, and/or the incubation mixture, is neutralized to a value within the pH range of 5.5 to 8 for bringing it into contact with the micro-organism.

Moreover, when the nitrogen containing heterocyclic compound to be treated is ONTA, the amine formed is stable and is not subject to any subsequent transformation while the pH of the incubation mixture is maintained at about 6.

When the solution of the nitrogen containing heterocyclic compound to be treated, or the incubation mixture, is at an acid pH outside the permissible range, the pH can be adjusted to a value that permits the conversion of the nitrogen containing heterocyclic compound to be treated using a base, this base being either in solution or a solid. Preferably, the base is a solid, so that the solution of nitrogen containing eterocyclic compound to be treated is not diluted. It can, for example, advantageously be in the form of pellets. This base can be chosen, for example, from within the group comprising NaOH and KOH.

According to the method of the invention, bringing the micro-organism into contact with the solution of the nitrogen containing heterocyclic compound to be treated is carried out at a temperature, preferably a substantially constant temperature that permits the culture of the micro-organism in an incubation mixture and the conversion of the nitro groups, that is to say, a temperature that is favorable to a culture of the micro-organism and to said conversion. When the micro-organism is a bacterium, in general, this temperature is between 20 and 35° C., preferably from 20 to 30° C. When the bacterium is *Bacillus licheniformis*, this temperature is preferably within the range 20 to 30° C. and more preferably at about 25° C.

The bringing into contact can be carried out for example in a fermenter, which can be a means of keeping the temperature substantially constant during the conversion of the nitro groups into amine groups.

In addition, the fermenter can be fitted with a stirrer to maintain agitation during the bringing into contact.

According to the method of the invention, an agent for inducing the general reducing metabolism of the micro-organism used can be added to the solution of the nitrogen containing heterocyclic compound comprising at least one nitro group, or to the incubation mixture, that brings it into contact with the micro-organism. This inducing agent is added to the solution or to the mixture to increase the general reducing metabolism of the micro-organism thereby encouraging the conversion of the nitro group or groups of the nitrogen containing heterocyclic compound into amine groups.

An optimum concentration of inducing agent for the general reducing metabolism can be determined by carrying out conversion tests on a nitrogen containing heterocyclic compound comprising a nitro group as a function of the concentration of inducing agent in an incubation mixture.

This inducing agent may be any compound that is able to induce the general reducing metabolism of the micro-organism used, for example, glucose, glucose polymers, molasses or maize hydrosylate etc.

When the agent for inducing the general reducing metabolism of the chosen micro-organism is glucose, its concentration in the solution can be, for example, about 0 to 3.0 g per 100 ml solution, preferably about 1 to 2 g per 100 ml of solution.

For example, for one liter of a solution of the nitrogen containing heterocyclic compound ONTA at 15 g/l, a biomass of *Bacillus licheniformis* of 90 g, a quantity of sugar of 15 g/l, a pH of about 6 and a temperature of 25° C., the method of the invention permits greater than 80% conversion of ONTA into the corresponding amine, and even all of it in 24 hours.

The method conforming to the invention therefore allows one to treat an aqueous industrial effluent comprising a toxic nitrogen containing heterocyclic compound to be treated, such as, for example ONTA. When the nitrogen containing heterocyclic compound to be treated has been converted by the micro-organism in the effluent to be treated into the corresponding amine, this treated effluent can, for example, be treated to remove the amine formed, by for example, gel filtration, for example on Sephadex G10.

The invention also relates to a method for the synthesis of 5-amino-1,2,4-triazole-3-one that comprises bringing a solution of 5-nitro-1,2,4-triazole-3-one into contact with a micro-organism capable of reducing the 5-nitro group into a 5-amino group.

The solution of 5-amino-1,2,4-triazole-3-one can be an aqueous solution of this compound, prepared at a concentration that can range up to the saturation concentration.

This method of synthesis can be carried out in the same manner as the method of converting a nitro group in a nitrogen containing heterocyclic compound to be treated according to the invention.

According to the method of the invention, the micro-organism can be selected by screening of micro-organisms that are living or are able to live in an industrial processing effluent arising from the manufacture of explosives, in foul water, and in a general way, in a medium, called in this description, a source medium, preferably comprising nitrogen containing heterocyclic compounds preferably comprising at least one nitro group.

For example, the screening can be carried out starting with a sample of a medium that can be treated according to the method of the invention.

According to the method of the invention, the micro-organism can be of the *Bacillus licheniformis* type.

According to the method of the invention, the *Bacillus licheniformis* is the *Bacillus licheniformis* colony LCM2 filed under number I-1915 in the CNCM held by the Pasteur Institute in France.

According to the invention, when the synthesis of 5-amino-1,2,4-triazole-3-one has been completed, it can be isolated from the mixture of solution and biomass by centrifugation to remove the biomass and by purification of the 5-amino-1,2,4-triazole-3-one contained in the supernatant liquid from the centrifugation.

The treatment can, for example, be carried out by evaporation of the aqueous phase and purification of the 5-amino-1,2,4-triazole-3-one extract by traditional purification methods.

The invention also relates to a colony of the *Bacillus licheniformis* type filed under the number I-1915 in the CNCM (Collection Nationale de Culture de Micro-organisms) held by the Pasteur Institute in France.

The characteristics and advantages of the invention will become more apparent on reading the description that follows. This description is directed towards an embodiment example of the invention given for the purposes of explanation, which is non-limitative and which refers to the appended figures.

DETAILED DESCRIPTION OF AN EMBODIMENT EXAMPLE OF THE INVENTION

In this example, an aqueous industrial processing effluent arising from the manufacture of explosives is being treated.

This aqueous industrial effluent contains ONTA with the following formula (III):

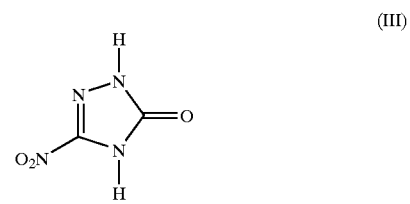

(III)

Screening of the Micro-organism and Preparation of the Biomass

Screening of the micro-organisms present in the aqueous industrial effluent mentioned above permitted the isolation of a *Bacillus licheniformis* colony. This colony has the advantage of being widespread in the natural environment and of not exhibiting any toxicity whatsoever. Furthermore, its use, according to the method of the invention does not require any special precautions whatsoever. It has been filed in the CNCM held by the Pasteur Institute under the number I-1915.

In order to form the biomass, this colony was cultivated at 25° C. for 48 hours in a rich, liquid culture medium with the following composition:

| $K_2HPO_4$ | 1 g | | |
|---|---|---|---|
| $KH_2PO_4$ | 0.5 g | | |
| glucose | 30 g | $NaNO_3$ | 2 g |
| maize liquor | 10 g | KCl | 0.5 g |
| $MgSO_4$ | 0.5 g | $FeSO_4$ | 0.02 g |

The medium is sterilized at 120° C. for 20 minutes.
The resulting culture was centrifuged in order to recover the *Bacillus licheniformis* biomass.

Determination of a pH that Permits the Conversion of the ONTA in the Aqueous Effluent A series of nine tests E1 to E9 were carried out as follows:
The following were added to and mixed in a fermenter, for example, a thermostated Erlenmeyer fermenter, the temperature of which was held at 25° C. and which included a stirring system regulated at 100 rpm:
  one liter of aqueous effluent including 15 g/l of ONTA and having a pH of 3.5
  90 g of *Bacillus licheniformis* biomass, and
  15 g of glucose to obtain an incubation mixture E having a pH of 3.5.

Test E1 was the control, it was carried out without modifying the pH of the incubation mixture E.

Tests E2 to E9 were carried out neutralizing the pH of the incubation mixture E with pellets of caustic soda in a way that provided for test E2, a pH of 5, for test E3, a pH of 5.5, for test E4, a pH of 6 and so on to test E9 in which the pH had been neutralized to obtain a pH of 8.5.

Each test was incubated at 25° C., with stirring at 100 rpm, for 10 days. At the end of the $10^{th}$ day, the quantity in g/l of ONTA in each incubation mixture was measured. Table 2 below shows the results obtained for tests E1 to E9:

TABLE 2

Determination of the pH that permits the conversion of ONTA

| Test | E1 | E2 | E3 | E4 | E5 | E6 | E7 | E8 | E9 |
|---|---|---|---|---|---|---|---|---|---|
| pH | 3.5 | 5 | 5.5 | 6 | 6.5 | 7 | 7.5 | 8 | 8.5 |
| [ONTA] g/l at the end of 10 days of incubation at 25° C. | 15 | 9.8 | 6.4 | 4 | 5.2 | 7.2 | 7.2 | 6.6 | 7.8 |

Figure 2:
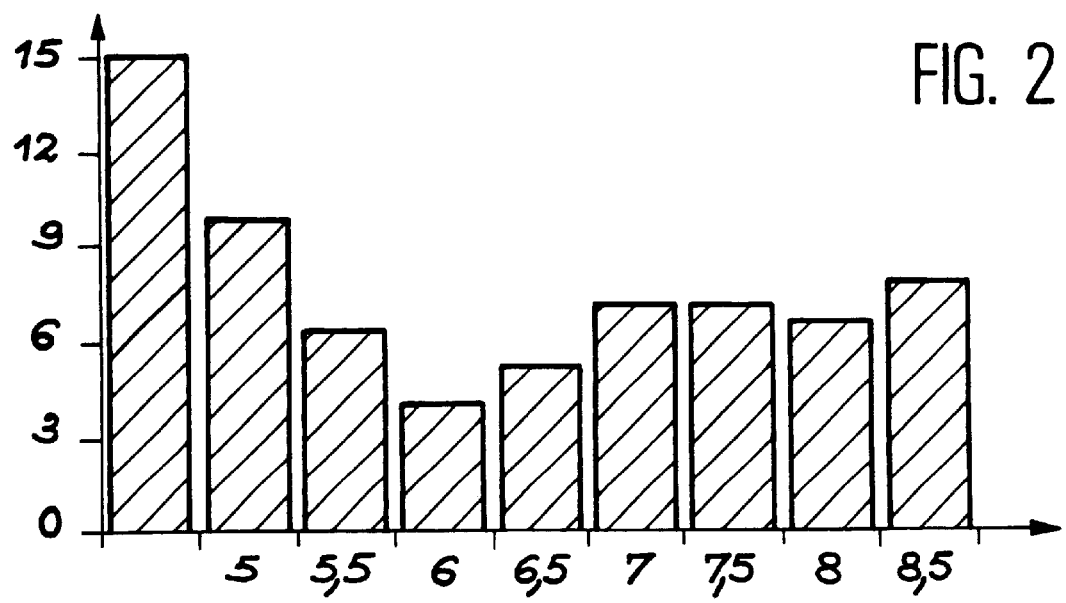
FIG. 2 is a graphical representation of the quantity in g/l of ONTA converted into the corresponding amine according to the method of the invention as a function of pH, for 10 days of incubation.

FIG. 2 was produced from the results in Table 2. It therefore illustrates the change in the concentration in g/l of ONTA in the incubation mixture as a function of the pH for 10 days of incubation.

These results show that the conversion of ONTA into the corresponding amine by *Bacillus licheniformis* is at its optimum for a pH of 6 for the incubation mixture, and that the pH that permits this conversion is a pH greater than 3.5, this pH advantageously being between 5.5 and 8.

Determination of an Optimum Concentration of an Agent for the Inducing of the General Reducing Metabolism of *Bacillus licheniformis*

A series of eight tests G1 to G8 were carried out starting with an incubation mixture produced as follows:

The following were added and mixed in a fermenter, for example, a thermostated Erlenmeyer fermenter, the temperature of which was held at 25° C. and which included a stirring system regulated at 100 rpm:
  one liter of aqueous effluent including 15 g/l of ONTA and having a pH of 3.5,
  caustic soda pellets in a way to obtain a pH of 6, and
  90 g of *Bacillus licheniformis* biomass to obtain an incubation mixture G having a pH of 6.

Test G1 was the control, it was carried out without adding any glucose to the incubation mixture G.

Tests G2 to G8 were carried out by adding glucose to the incubation mixture G in a way to provide in these tests a glucose concentration ranging from 0.5 g (test G2) to 10 g (test G8) of glucose for 100 ml of incubation mixture G.

Each test was incubated at 25° C., with stirring at 100 rpm for 7 days. At the end of the $7^{th}$ day, the quantity of amine in g/l formed by conversion of ONTA in the incubation mixture was measured. Table 3 below shows the results obtained for tests G1 to G8.

TABLE 3

Determination of an optimum quantity of glucose for the conversion of ONTA

| Test | G1 | G2 | G3 | G4 | G5 | G6 | G7 | G8 |
|---|---|---|---|---|---|---|---|---|
| [glucose] | 0 | 0.5 | 1 | 1.5 | 2 | 3 | 5 | 10 |
| g/l of amine formed at the end of 7 days of incubation at 25° C. | 2.1 | 4.75 | 6.25 | 8.35 | 9.65 | 9.65 | 13.3 | 10.6 |
| uncertainty in g/l | 0.6 | 0.05 | 1.15 | 1.65 | 1.15 | 0.55 | 0.3 | 1.5 |

Figure 3:
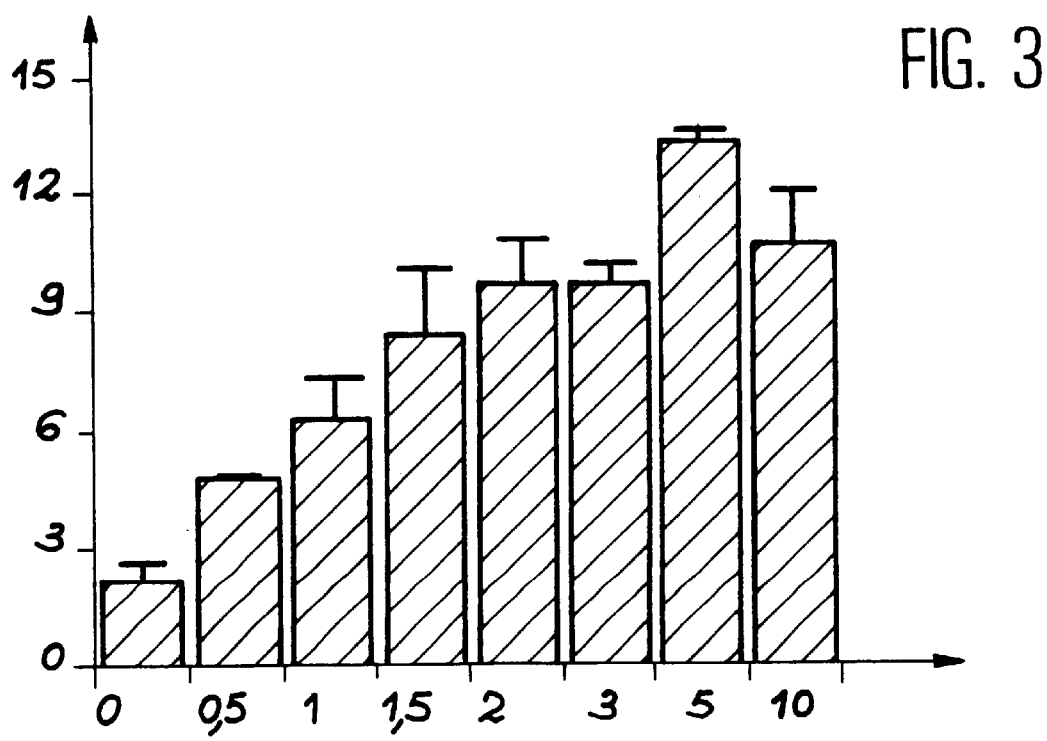
FIG. 3 is a graphical representation of the quantity in g/l of the amine formed by the conversion of ONTA according to the method of the invention, as a function of the concentration of glucose, for 7 days of incubation.

FIG. 3 was produced from the results in Table 3. It therefore illustrates the changes in the concentration of amine in g/l formed by conversion of ONTA as a function of the concentration of glucose in g/100 ml of incubation mixture for 7 days of incubation.

These results show that the conversion of ONTA into the corresponding amine by *Bacillus licheniformis* is a maximum for a concentration of glucose of 5 g/100 ml of incubation mixture.

Taking into account a search for a compromise between the effectiveness and the cost of the method according to the invention, the inventors have chosen to use in the example below, a concentration of 15 g of glucose per liter of incubation mixture.

Conversion of the ONTA Contained in the Industrial Effluent by a Micro-organism

In a thermostated fermenter that includes a stirring system, one liter of aqueous effluent to be treated was neutralized to pH 6 using caustic soda pellets, with stirring at 100 rpm.

90 g of the *Bacillus licheniformis* biomass previously formed was added to this neutralized solution together with 15 g of glucose to induce the general reducing metabolism of *Bacillus licheniformis*. This incubation mixture was held, with stirring at 100 rpm, for 72 hours at 25° C. and the conversion of the nitro group of the ONTA into amine was followed by measuring by high performance liquid chromatography, as a function of time, the changes in the concentrations of the ONTA and the amine formed.

Figure 1:
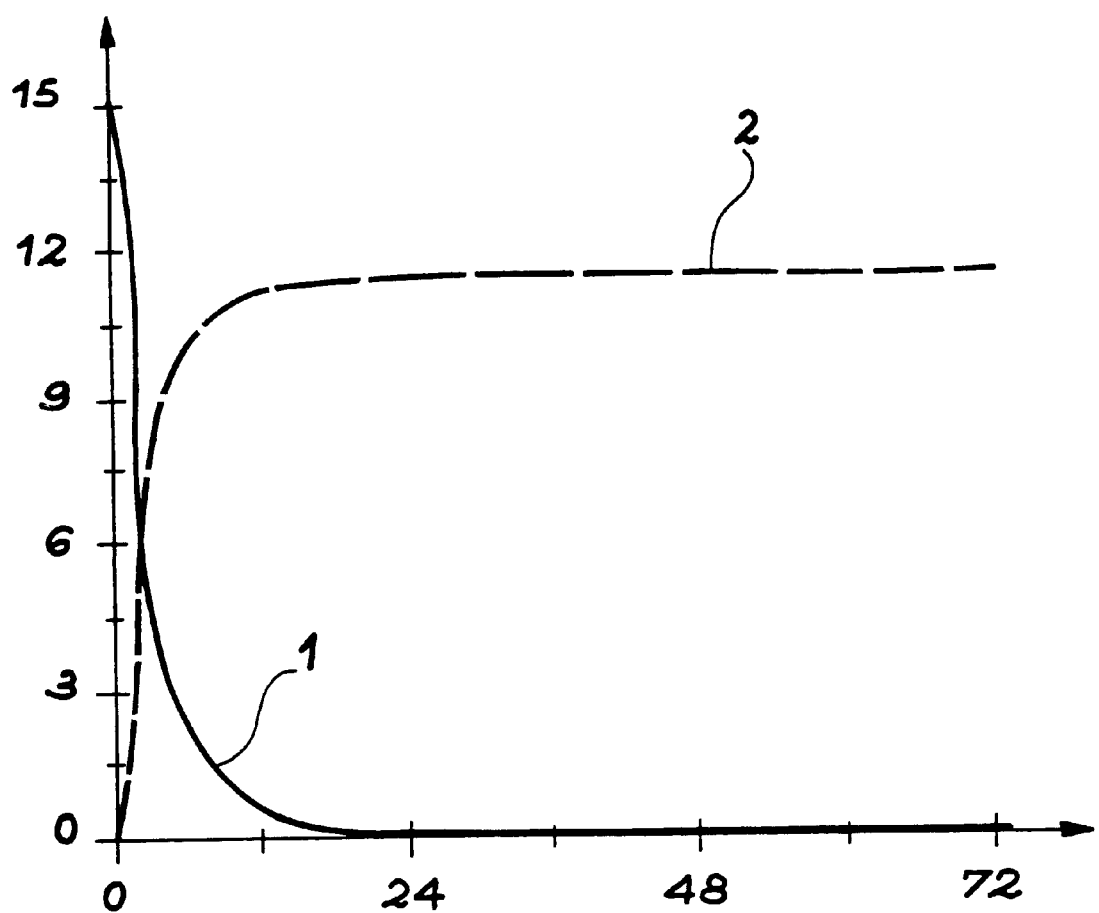
FIG. 1 is a graphical representation of the conversion of ONTA into 5-amino-1,2,4-triazole-3-one that illustrates the changes in the concentration in g/l of these two compounds as a function of time in hours in an example of the implementation of this invention on an effluent treated with *Bacillus licheniformis* (colony No. I-1915 in the CNCM).

In FIG. 1, curve 1 is the curve that illustrates the conversion of ONTA and curve 2 is the curve illustrating the formation of the corresponding amine.

These curves show that all of the explosive ONTA contained in the initial solution was converted into non-explosive amine in 24 hours.

Moreover, curve 2 shows that the amine formed does not undergo any subsequent transformation when the pH is held at 6.

At the end of 72 hours, the mixture was centrifuged at 18000 g to separate the biomass from the solution. The solution obtained was purified after freeze drying, by taking it up in methanol, and after evaporation of the methanol, taking it up in a reduced volume of water to obtain a concentrated solution.

The purification of the amine was carried out by elution with water on a SEPHADEX G 10 gel column. Since the amine formed is a yellow color, it was easy to follow its elution. The eluent water was then evaporated and the amine recovered in the form of a yellowish powder having the chemical properties given in Table 4 below:

TABLE 4

| | Properties of the amine formed |
|---|---|
| Melting point | 240–245° C. |
| NMR$^{13}$C | (DMSO, 300 MHz)δ: 155.1 (C=O), 147.8 (C=N) |
| IR | 3684, 3620, 3023, 2980, 2889, 2403, 1525, 1469, 1216, 1040, 920 |
| MSIE | 100(M$^+$, 83), 57(35), 43(100), CIMS: m/z 101 (M + H$^+$) |
| Anal. | C$_2$H$_4$N$_4$O, Calc. C, 24; H, 4; N, 55; 0, 16. Found C, 24.6; H, 3.8; N, 54.1; 0, 17.4 |

This amine with the formula (IV) below:

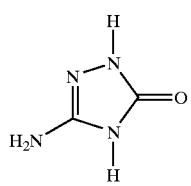

(IV)

obtained from the ONTA in the effluent is of interest since it can be exploited.

Moreover, since the *Bacillus licheniformis* colony is not toxic, the treated effluent, from which the explosive ONTA has been extracted and converted into a non-explosive amine showed no toxicity so that it could be released into the natural environment without presenting any major risks to the environment.

Conversion of the ONTA Contained in the Aqueous Industrial Effluent by Hydrogenation in the Presence of Pd/C 40 ml of effluent containing 1.3 g of ONTA were mixed with 140 mg of Pd/C (10%) in a reactor that includes a stirring system. The mixture was hydrogenated using a PARR apparatus at a pressure of 0.21 MPa (30 psi) at ambient temperature for 5 hours. The mixture was analyzed by HPLC during the course of the reaction to convert the ONTA in order to follow the course of this reaction.

It was possible to convert all of the ONTA into the corresponding amine.

It should be noted that, after filtration of the mixture and evaporation of the solvent, that is to say, the water, 0.7 g of amine was obtained.

The spectroscopic and structural characteristics are identical to those described in the example in which the reducing agent was *Bacillus licheniformis* LCM2. This conversion was also carried out in a methanol solution and gave the same results as in aqueous solution.

What is claimed is:

1. A method for converting a nitro group into an amine group of a compound present in a solution, wherein said compound has the following formula (I):

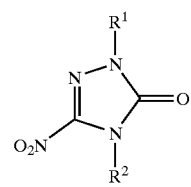

(I)

wherein
R$^1$ and R$^2$ are independently selected from the group consisting of hydrogen, —NO$_2$, —OH, —COOH, —Cl, —NH$_2$, cyclic glucose units and linear glucose units, wherein the cyclic and linear glucose units are optionally substituted by one or more groups selected from the group consisting of acetyl, tolyl, linear alkyl groups having from 1 to 10 carbon atoms and cyclic alkyl groups having from 1 to 10 carbon atoms, wherein the linear and cyclic alkyl groups are optionally substituted with one or more groups selected from the group consisting of —NO$_2$, —OH, —COOH, —Cl, and —NH$_2$; said method comprising the following steps:
   a) bringing said solution of compound (I) into contact with a *Bacillus licheniformis* which is capable of converting the nitro group into an amime group thereby converting one nitro group of compound (I) into an amine group in the solution; and
   b) separating the *Bacillus licheniformis* from the solution obtained after step a).

2. The method according to claim 1, in which *Bacillus licheniformis* is *Bacillus licheniformis* LCM2 deposited under the number I-1915 in the CNCM.

3. The method according to claim 1, in which in compound (I), R$^1$ and R$^2$ are both hydrogen.

4. The method according to claim 1, further comprising the step of maintaining the solution of compound (I) at a pH value within the range 5.5 to 8 before bringing it into contact with *Bacillus licheniformis*.

5. The method according to claim 1, in which step a) is carried out at a temperature that permits the growth of *Bacillus licheniformis*.

6. The method according to claim 1, further comprising the step of adding a source of energy for *Bacillus licheniformis* to the solution of compound (I) before step a).

7. The method according to claim 6, in which the source of energy is chosen from the group consisting of glucose, glucose polymers, molasses and maize hydrolysates.

8. The method according to claim 1, in which the solution of compound (I) is a processing effluent arising from the manufacture of explosives.

9. A method for manufacturing 5-amino-1,2,4-triazole-3-one from 5-nitro-1,2,4-triazole-3-one by converting the 5-nitro group to a 5-amino group, said method comprising the following steps:
   a) bringing a solution of 5-nitro-1,2,4-triazole-3-one into contact with *Bacillus licheniformis* in order to convert the 5-nitro group into a 5-amino group, and b) separating the *Bacillus licheniformis* from the solution obtained after step a).

10. A method for converting a nitro group into an amine group of a compound present in a solution, wherein said compound has the following formula (I):

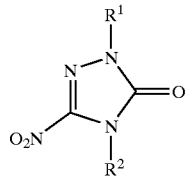
(I)

wherein $R^1$ and $R^2$ are independently selected from the group consisting of hydrogen, —$NO_2$, —OH, —COOH, —Cl, —$NH_2$, cyclic glucose units and linear glucose units; said method comprising the following steps:

a) bringing said solution of compound (I) into contact with a *Bacillus licheniformis* which is capable of converting the nitro group into an amine group thereby converting one nitro group of compound (I) into an amine group in the solution; and b) separating the *Bacillus licheniformis* from the solution obtained after step a).

* * * * *

UNITED STATES PATENT AND TRADEMARK OFFICE
CERTIFICATE OF CORRECTION

PATENT NO. : 6,582,952 B1
DATED : June 24, 2003
INVENTOR(S) : Laurence Le Campion et al.

It is certified that error appears in the above-identified patent and that said Letters Patent is hereby corrected as shown below:

Column 12,
Line 35, delete the word "amime" and insert therefore -- amine --.

Signed and Sealed this

Ninth Day of September, 2003

JAMES E. ROGAN
*Director of the United States Patent and Trademark Office*